United States Patent [19]

Mazloomdoost et al.

[11] Patent Number: 5,072,726
[45] Date of Patent: Dec. 17, 1991

[54] VAPORIZER FOR INHALATION ANESTHETICS DURING HIGH-FREQUENCY JET VENTILATION AND ASSOCIATED METHOD

[75] Inventors: Manoochehr Mazloomdoost, Lexington, Ky.; Wilfred L. Foon, Pittsburgh, Pa.

[73] Assignee: University of Pittsburgh of the Commonwealth System of Higher Education, Pittsburgh, Pa.

[21] Appl. No.: 613,981

[22] Filed: May 11, 1990

Related U.S. Application Data

[63] Continuation of Ser. No. 107,224, Oct. 9, 1987, abandoned.

[51] Int. Cl.⁵ ............................................. A61M 11/00
[52] U.S. Cl. ........................... 128/200.14; 128/200.21; 128/203.12
[58] Field of Search ...................... 128/200.14, 200.18, 128/200.21, 203.12, 203.25

[56] References Cited

U.S. PATENT DOCUMENTS

| | | | |
|---|---|---|---|
| 2,785,679 | 3/1957 | Wallschleger | 128/200.18 |
| 4,233,842 | 11/1980 | Raemer et al. | 128/719 |
| 4,280,494 | 7/1981 | Cosgrove, Jr. et al. | 604/50 |
| 4,527,558 | 7/1985 | Hoenig | 128/910 |

*Primary Examiner*—Edgar S. Burr
*Assistant Examiner*—Aaron J. Lewis
*Attorney, Agent, or Firm*—Arnold B. Silverman; Craig G. Cochenour; Suzanne Kikel

[57] ABSTRACT

A vaporizer that may be used in high-frequency jet ventilation (HFJV) is disclosed. The vaporizer operates on the principle of airblast atomization. The vaporizer provides inhalation anesthesia and is adaptable to the high pressure requirements of a high frequency jet ventilator. The apparatus consists of a main tube or body which defines a passageway. Vaporization occurs by the principle of airblast atomization inside the passageway. The open end of the main body adapts to a connector of the endotracheal tube. A gas supply needle extends into and is centered within the lumen of the main body and directed along the axis of the body. The gas supply needle may be positioned horizontally and gas is jetted through it from a high-frequency jet ventilator. An inhalation anesthetic supply needle intersects the main body in general proximity to the gas supply needle. Preferably the inhalation anesthetic supply needle intersects the main body in a generally perpendicular manner to the gas supply needle. At the point of intersection of the inhalation anesthetic supply needle and the gas supply needle airblast atomization occurs. Inhalation anesthetic is drawn up into the inhalation anesthetic supply needle by the negative pressure that is created by the high velocity flow of the gas at the tip of the gas supply needle.

33 Claims, 3 Drawing Sheets

VAPORIZER FOR INHALATION ANESTHETICS DURING HIGH-FREQUENCY JET VENTILATION AND ASSOCIATED METHOD

This is a continuation of application Ser. No. 07/107,224 filed Oct. 9, 1987, now abandoned.

BACKGROUND OF THE INVENTION

1. Field Of The Invention

This invention relates to a vaporizer and more specifically it relates to a vaporizer for use with a high-frequency jet ventilator and an associated method.

2. Brief Description Of The Prior Art

High-Frequency Jet Ventilation (HFJV) is one of the newer methods of artificial ventilation used in the operating room with application of preventing aspiration, and ventilating patients suffering from broncho-plural fistula, for example. Example of a high-frequency jet ventilators that may be used is U.S. Pat. No. 4,471,773.

Presently in the operating room during surgery, HFJV can be used only when balanced anesthesia is administered. Balanced anesthesia is the use of narcotics and/or nitrous oxide with muscle relaxant drugs. Balanced anesthesia has some disadvantages in treatment of hypoxemic patients, for example, namely a high percentage of oxygen in excess of about fifty percent (50%) cannot be used.

Balanced anesthesia does not provide the broncho-dilating effect of inhalational anesthetics and awareness under anesthesia has been reported more frequently during balanced anesthesia than inhalation anesthesia.

Ordinary vaporizers normally used in anesthesia machines or ventilators can not be used because of the high pressure (20 to 50 p.s.i.) that is required during HFJV. U.S. Pat. No. 3,040,742 discloses an oxygen tent controlled inhalation therapy that contains an adjustable nozzle. An apparatus that jets respiratory gas from a ventilator is known. See U.S. Pat. No. 4,537,188.

Various patents disclose various constructions of atomizers to supply medicine to a patient. See U.S. Pat. Nos. 2,906,463 and 4,318,397. Inhalers which contain a vapor producing unit and a vapor feeding nozzle are also known. See U.S. Pat. No. 4,456,007. Apparatus for artificial respiration are also known. See U.S. Pat. No. 4,495,946. Various types of nebulizers which entrain small liquid particles in a stream of gas are known. See U.S. Pat. Nos. 3,040,742; 3,104,062; 3,172,406; 3,379,194; 3,809,080; and 4,344,574.

There remains, therefore, a very real and substantial need for a vaporizer that is compatible with high-frequency jet ventilation for use of inhalation anesthesia.

SUMMARY OF THE INVENTION

The present invention provides a vaporizer that may be used with high-frequency jet ventilation (HFJV). The vaporizer operates on the principle of airblast atomization which causes instant vaporization of a fluid during HFJV. According to the principles of airblast atomization when a gas such as air or oxygen is passed with a high velocity over a thin layer of fluid, the fluid is disintegrated into droplets of about several microns in diameter. These droplets are then dispersed with a stream of gas and evaporate substantially instantaneously due to substantial increase in surface area.

The apparatus consists of a main tube or body. The open end of the main body adapts to a connector of the endotracheal tube. A gas supply needle is centered within the lumen of the main body and directed along the axis of the body. The gas supply needle is connected to the high pressure jet ventilator. Jetting occurs through this needle, which provides ventilation and airblast atomization. An inhalation anesthetic supply needle intersects the main body in the general proximity of the gas supply needle. Preferably, the needles are generally perpendicular to each other. The tip of the inhalation anesthetic supply needle is preferably below the gas supply needle. The cross-section of the needles are generally perpendicular or at a generally right angle. The tip of the inhalation anesthetic supply needle preferably stands against about the lower third of the diameter of the tip of the gas supply needle. It is also preferred that the gas supply needle be larger than the inhalation anesthetic supply needle.

The inhalation anesthetic supply needle is connected to an infusion pump means which infuses fluid anesthetic. Preferably, the inhalation anesthetic supply needle intersects the main body in a generally perpendicular manner to the gas supply needle. A scavenging tube intersects the main tube from below the main body and is preferably generally parallel to the inhalation anesthetic supply needle. The scavenging tube defines a passageway which connects the vaporizer to a respirometer and a scavenging system for evacuation of exhaled gases. A respirometer may be disposed between the vaporizer and the scavenging system to measure minute volume.

The gas supply needle may be positioned horizontally and gas is jetted through it from the high-frequency jet ventilator. At the point of intersection of the inhalation anesthetic supply needle and the gas supply needle, airblast atomization occurs. An inhalation anesthetic, such as enflurane, is drawn up into the inhalation anesthetic supply needle by the negative pressure that is created by the high velocity flow of the gas at the tip of the gas supply needle.

Optionally, the vaporizer has connecting means such as an endotracheal tube that provides the inhalation anesthesia to the patient's lungs from the vaporizer.

Optionally, a reinspired gas tube may be disposed generally perpendicular to the main body. This tube is used in circle system anesthesia. Circle system anesthesia recirculates expired air from the scavenging tube back into the flow of anesthesia. This tube may be used for accepting reinspired gases if the vaporizer is to be used in semi-closed circle anesthesia. This tube is not required if the vaporizer is used in a non-rebreathing system.

It is an object of the present invention to provide a vaporizer which is compatible with high-frequency jet ventilation.

It is another object of the present invention to provide a vaporizer that provides inhalation anesthesia for high-frequency jet ventilation.

It is a further object of the present invention to provide a vaporizer which operates on the principle of airblast atomization.

It is another object of the present invention to provide a vaporizer which comprises a body with a passageway extending therethrough and contains the tips of two needles that are in generally close proximity which provide inhalation anesthesia.

It is a further object of the present invention to provide a method of ventilating a patient utilizing the vaporizer of the present invention.

These and other objects of the invention will be more fully understood from the following description of the invention in reference to the illustrations appended hereto.

DESCRIPTION OF THE PREFERRED EMBODIMENTS

Figure 1:
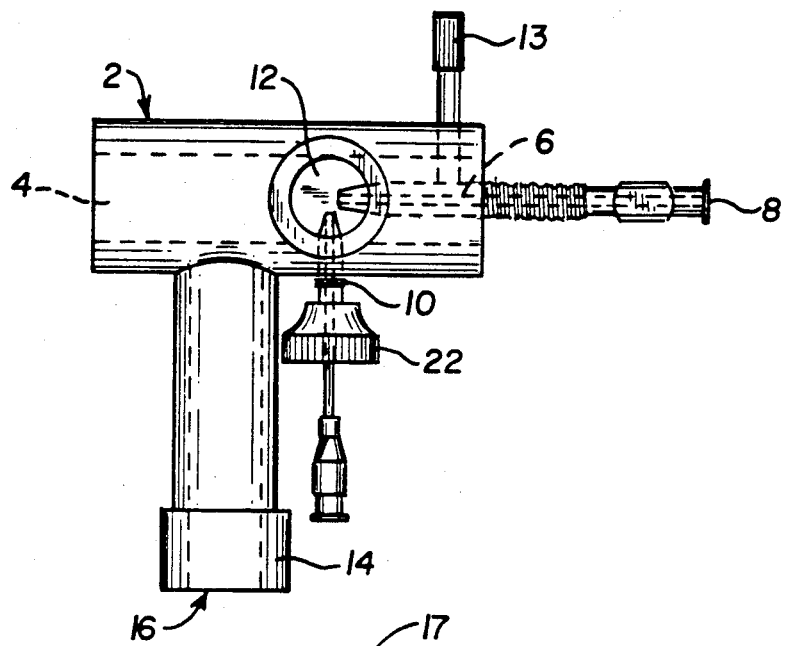
FIG. 1 shows front elevational view of a vaporizer of the present invention.

As used herein, the term "patients" includes any member of the animal kingdom including but not limited to human beings.

High-frequency jet ventilation (HFJV) has been used only with balanced anesthesia because heretofore there has been no vaporizer available for inhalation anesthetic using this method of ventilation. The prior art vaporizers are not compatible with HFJV due to the high pressures such as 20 to 50 p.s.i. required during HFJV.

The vaporizer of the present invention operates on the principle of airblast atomization. According to this principle, whenever a gas such as air or oxygen is passed with high velocity over a thin layer of fluid, such as water or enflurane, the fluid disintegrates into very small droplets several microns in diameter. These droplets are then dispersed with a stream of gas and evaporate substantially instantaneously due to the substantial increase in the surface area. For example, water droplets of 10 $\mu$ in diameter evaporate within 60 milliseconds at 20° C. The boiling point of enflurane is 56.5° C., as compared with 100° C. for water at 1 atmospheric pressure under standard conditions. The lower boiling point would be expected to cause more rapid evaporation at a given temperature. The latent heat of enflurane is 42 cal/g. whereas the latent heat of water is 537 cal/g. More efficient evaporation occurs when less cooling occurs. A lower latent heat leads to less surrounding heat loss during airblast atomization of enflurane when compared to water.

FIGS. 1-4 illustrate various views of a preferred form of the vaporizer of the present invention. In FIGS. 1-4, a main body 2 defines an elongated passageway 4. The left side of main body 2 is preferably open ended. Its inside diameter is preferably ⅜ inches. This opening size adapts to the connector of a standard endotracheal tube at the other end of the main body 2. A gas supply needle 6 extends into passageway 4. Gas supply needle 6 is preferably an 8 to 14 gauge needle, and more preferably a 14 gauge needle. Gas supply needle 6 is centered within the lumen or passageway 4 of main body 2 directed along its axis. The gas supply needle may be optionally threaded 7. The outside end of the gas supply needle 8 is connected to the high-frequency jet ventilator (not shown).

An inhalation anesthetic supply needle 10 intersects passageway 4 in generally close proximity to gas supply needle 6. In the preferred embodiment shown, the inhalation anesthetic supply needle 10 is generally perpendicular to the gas supply needle 6. The inhalation anesthetic supply needle 10 preferably enters main body 2 from below and intersects the gas supply needle 6 at about a 90° angle. Preferably, inhalation anesthetic supply needle 10 is smaller than the gas supply needle 6. The inhalation anesthetic supply needle is about an 18 to 22 gauge needle, and more preferably a 20 gauge needle.

The distance between the two needles is preferably about 0.3 to 1.0 mm and more preferably about 0.6 mm. It is further preferred that the tip of the inhalation anesthetic supply needle 10 be placed between about the top third to the bottom third of the diameter of the tip of the opening of the gas supply needle 6. More specifically, the tip of the inhalation anesthetic supply needle 10 is oriented generally aligned with the longitudinal central axis of the gas supply needle 6. The center of the opening of the inhalation anesthetic supply needle 10 is positioned within about half of the radius of the opening of gas supply needle 6.

Gas from the high-frequency jet ventilator (not shown) is jetted through the gas supply needle 6. Jetting of the gas ventilates the patient. Meanwhile, an inhalation anesthetic is injected into the gas stream through the inhalation anesthetic supply needle 10. The inhalation anesthetic, which may be any inhalation anesthetic such as enflurane, fluothane, isoflurane, and the like, is infused through the inhalation anesthetic supply needle 10 from an infusion pump means (not shown). The inhalation anesthetic is drawn up into the tip of the inhalation anesthetic supply needle by negative pressure that is created by the high velocity flow of gas at the tip of the gas supply needle 6. The flow of the inhalation anesthetic is accurately controlled by an infusion pump means (not shown).

The distance between the tip of the gas supply needle 6 and the tip of the inhalation anesthetic supply needle 10 may be adjusted by rotating the gas supply needle 6. The adjustment of the intersection tips of these needles may be effected by rotating the inhalation anesthetic supply needle. Alternatively, the needle size and distance may be fixed.

Optionally, stabilizing means such as pin 13, as shown in FIG. 1, stabilizes the gas supply needle 6. A plastic washer at the tip of pin 13 may be used to prevent damage to the gas supply needle 6. Optionally, pin 22 may be associated with the inhalation anesthetic supply needle 10. Stabilizing means such as pin 22, allows the inhalation anesthetic supply needle 10 to enter the main body 2 through it. Preferably, the tip of the inhalation anesthetic supply needle 10 is encased with a stabilizing means such as a washer inside the wall of main body 2. Pin 22 and the washer serve to stabilize and limit movement of the inhalation anesthetic supply needle 10. Rotating pin 22 squeezes the washer which holds inhalation anesthetic supply needle 10 tightly in position.

The tip of the two needles 6, 10 may be visualized through a window 12 in the wall of main body 2. The window or portal 12 allows visualization of the needle tips and observation of the atomization site. The needles 6, 10 may be adjusted by adjustment means. The window 12 enables one to adjust the needles to the appropriate position and to view the atomization.

Optionally, a scavenging tube 14 enters the main body 2. Preferably the scavenging tube 14 enters main body 2 from below on a vertical plane and is preferably generally parallel to the inhalation anesthetic supply needle 10. The tube 14 defines a lumen or passageway 16. Tube 14 serves to connect the vaporizer with a scavenging system and/or a respirometer. In the case of a non-rebreathing system of anesthetizing of patient, the scavenging system evacuates the expired patient gases to outside the operating environment. It is preferred that the outside diameter of scavenging tube 14 be about 7/8 inch to accommodate standard respirometers and/or evacuation hoses.

Figure 2:
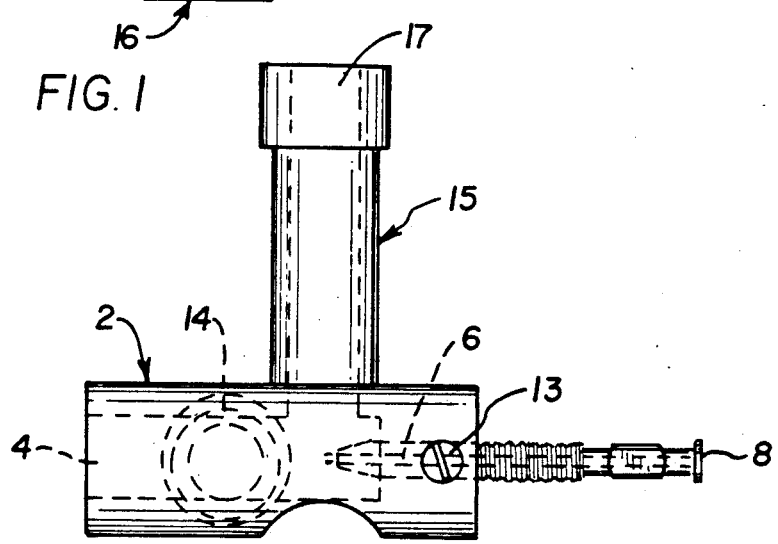
FIG. 2 shows a top plan view of the vaporizer of of FIG. 1.
Figure 3:
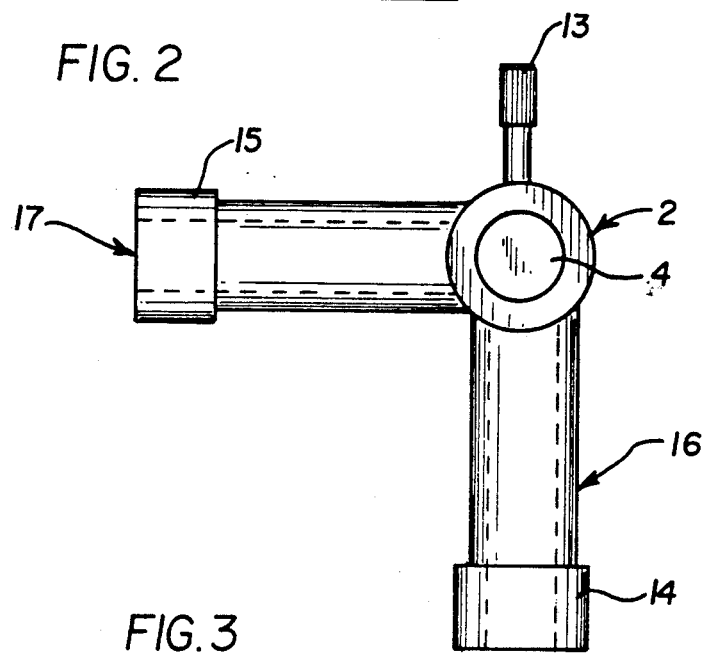
FIG. 3 shows a lewft side plan view of a vaporizer of FIG. 1.
Figure 4:
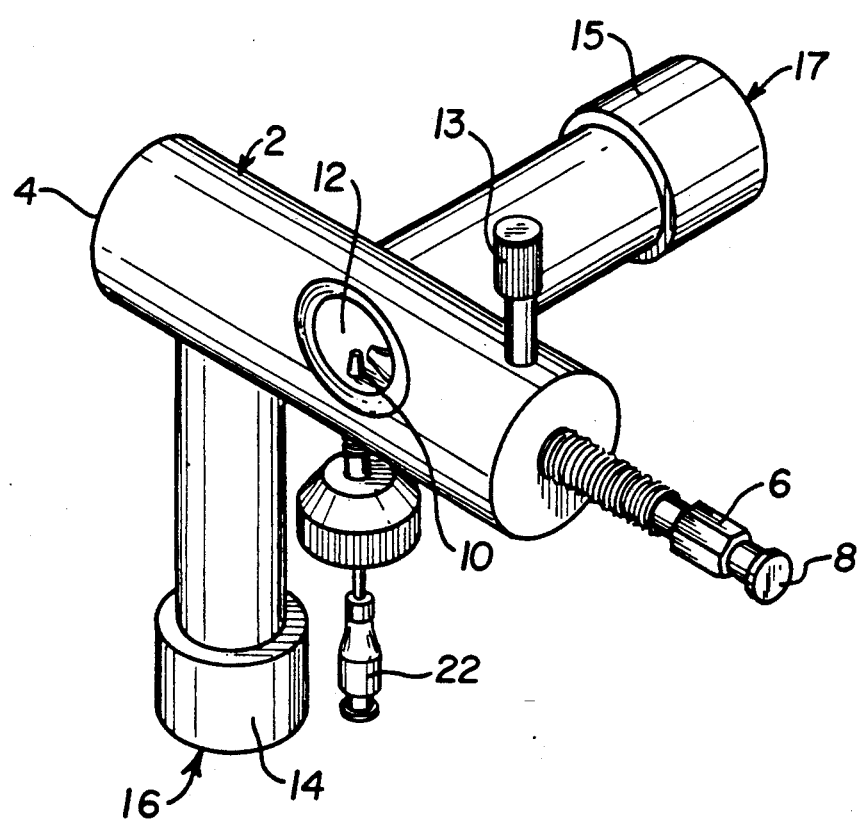
FIG. 4 shows a perspective view of a vaporizer of the present invention.

Referring more specifically to FIGS. 2 and 4, reinspired gas tube 15 which defines passageway or lumen 17, may included when a circle system is used. The circle system recirculates expired air that has passed through scavenging tube 14 back into reinspired tube 15 and then into the stream of gas entrained with inhalation anesthetia. This system minimizes contamination of the gas. Preferably, the reinspired gas tube 15 is opposite the window 12 and is generally perpendicular to the main body 2. The reinspired gas tube 15 is connected to the scavenging tube 14 by means of tubing. Optionally, dessicant material such as calcium hydroxide or sodium hydroxide may be placed in the tubing to absorb carbon dioxide gas present in the expired gases.

Figure 5:
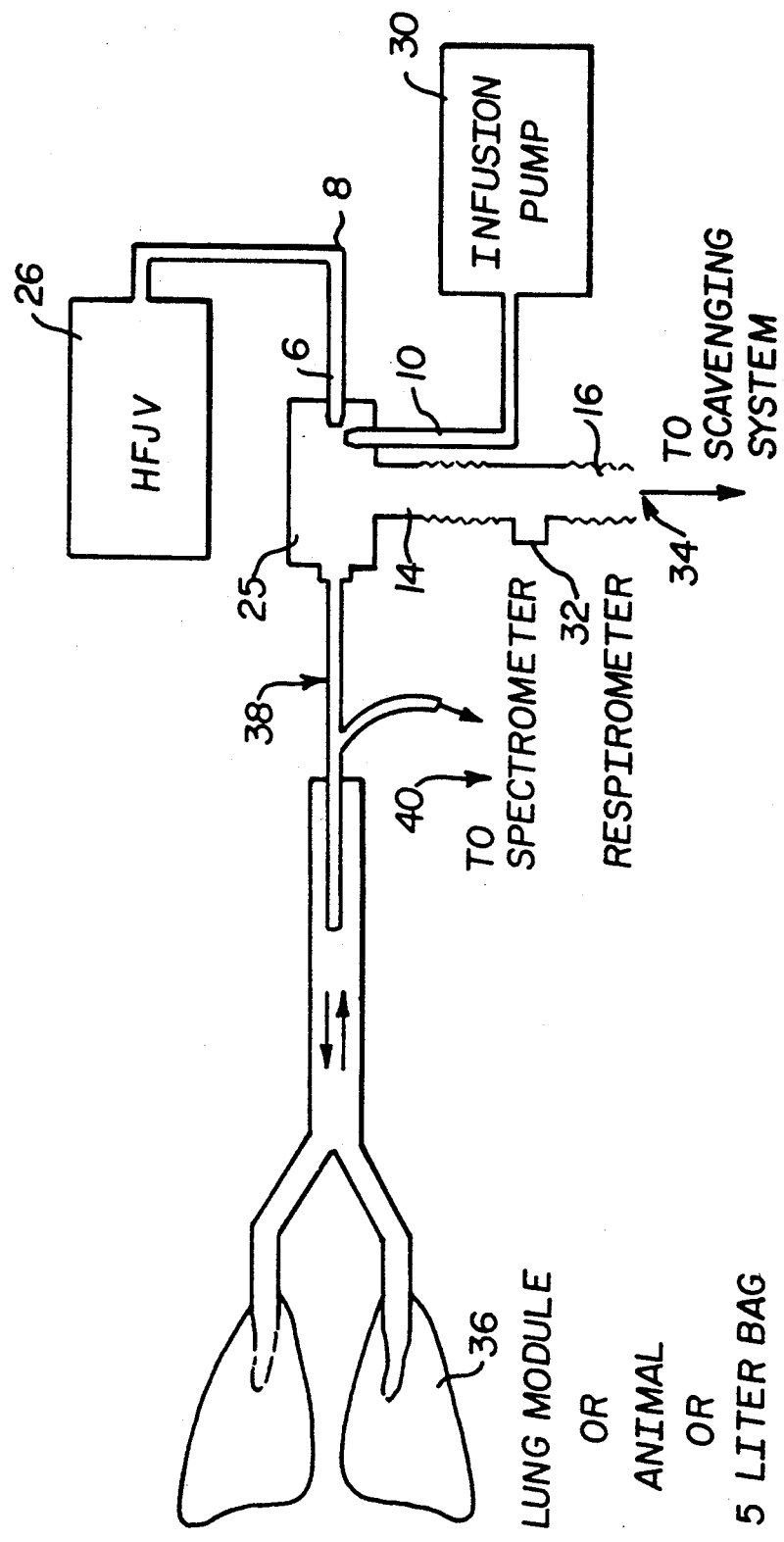
FIG. 5 is a schematic diagram of the vaporizer of the present invention as incorporated into a high-frequency jet ventilation system.

Referring to FIG. 5, the main body 2 of the vaporizer 25 is preferably maintained in a generally horizontal plane at the time of function and vaporization occurs inside the main body 2. The gas supply needle 6 is preferably on a generally horizontal plane and allows gas to be jetted through it from the high-frequency jet ventilator 26. Jetting maintains the function of ventilating the patient. The outside end 7 of the first needle 6 is connected to the high frequency jet ventilator 26. The ventilator 26 jets or intermittantly pushes air or oxygen into the lungs of an animal or human. The ventilator 26 jets gas, preferably air or oxygen at a rate of up to 150 times per minute for a human patient. Animal patients may have a rate of up to 2000 times per minute. The jetting allows the gas with entrained inhalation anesthetic to pass into the lungs of the patient 36. Passive exhalation replaces the spontaneous breathing of the patient. This function assists delivery of air or oxygen to the patient and eliminates excess carbon dioxide. After exhalation, the expired air flows from the lungs to the vaporizer 25 and into scavenging tube 14.

The flow of the inhalation anesthetic is accurately controlled by an infusion pump means 30 connected to the outside end of the inhalation anesthetic supply needle 10. The infusion pump means 30 provides an accurate control of inhalation anesthetic. Inhalation anesthetic is continually infused through the inhalation anesthetic supply needle 10 at a rate of about 0 to 30 ml/min. By adjusting the ratio of infused inhalation anesthetic to minute volume, the percentage of inspiratory concentration is determined. Minute volume is the amount of gas moved into and out of the lungs of the patient by the ventilator. Minute volume is equal to the liters of gas flowing to the lung of the patient.

Scavenging tube 14 is connected to a respirometer 32 by means of a hose. The respirometer 32 measures minute volume in units of liters per minute. The respirometer 32 measures the volume of gas that passes through scavenging tube 14. The other end of the respirometer 32 is attached to a hose which will allow expiratory gases to exit through the scavenging system 34. The scavenging system 34 permits excess exhaled gases to exit from the vaporizer and prevents contamination of the surrounding atmosphere. The scavenging system is preferably an evacuating means that draws expired gases away from the vaporizer 25.

The patient's lungs 36 are connected to the system by means of an endotracheal tube 38, and more preferably a hi-lo tube. An endotracheal tube 38 is generally a flexible plastic tube which is inserted into the trachea. The open end of this tube is connected to the vaporizer 25 and ventilator 26 which maintains the function of breathing by pushing ventilating gases in and out of the patient's lungs. If a hi-lo tube is used, optionally, a mass spectrometer 40 may be attached to a side port of the high-lo tube to analyze the concentration of the gases. The mass spectrometer 40 determines the concentration of the inhalation anesthetic, patient gases, and certain other gases inside the hi-lo tube. The hi-lo tube 38 may also have a port that measures pressure inside the endotracheal tube 38.

A patient is ventilated by preparing the patient and connecting the patient by means of an endotracheal tube to the vaporizer. The vaporizer is connected to a high-frequency jet ventilator. Gas is jetted through the gas supply needle from the HFJV. Inhalation anesthetic is infused from an infusion pump means through the inhalation anesthetic supply needle and entrained in the jetted gas stream by means of airblast atomization. This entrained gas is passed to the patient's lungs. The gas with entrained fluid is passed through the endotracheal tube to the patient's lungs. By passive exhalation the patient expires the gas which passes through the endotracheal tube into the vaporizer between jets of gas. This expired gas is passed into the scavenging tube where the respirometer may measure minute volume. Optionally, the patient's expired air may be analyzed by means of a mass spectrometer.

EXAMPLE

Eight dogs of either sex, weighing 18-22 kg were anesthetized with 10 mg/kg IV thiopental and immobilized with 80 ug/kg of pancuronium bromide (Pavulon, Organon, Inc.). They were intubated and ventilated (Harvard Ventilator Model #607, Harvard Apparatus, Inc.) and EKG leads were attached. Pulmonary artery, femoral artery, and femoral venous catheters were inserted. Ventilation was then switched to HFJV (Model VS600, Industrial Development Co., Pittsburgh, PA). Fixed ventilator settings chosen were: driving pressure, 20-50 psi as needed to provide adequate minute volume and $CO_2$ elimination; inspiratory time, 30% of respiratory cycle rate, 150 breaths/min; and $F_iO_2 = 1.00$ (100% oxygen). Baseline measurements of mean arterial blood pressure (MAP), cardiac output, and arterial blood gases were made. The minute volume was measured and liquid enflurane infusion into the vaporizer was begun with an infusion pump (Sigma Co., St. Louis, MO). The rate of infusion was adjusted to the minute volume to obtain an inspired enflurane concentration of 2.2% as measured by mass spectrometry. The minute volume and infusion rate was kept constant throughout the 120 min. of the experiment. All monitored physiological variables were recorded every 15 min. after beginning enflurane infusion. Arterial and venous blood enflurane levels were measured at 5, 15, 30, 60, 90, and 120 minutes. Residual muscle relaxation was reversed by 1 mg Exactly 1.0 ml of whole blood was added to pre-weighed screw-top test tubes containing 1.0 ml toluene with chloroform as an internal standard. The tubes were capped immediately, vigorously agitated, and placed on a rocking shaker for 30 min. One ul of the sample was injected into a Model 3700 Varian gas-liquid chromatograph with a flame ionization detector and a 6-ft glass column packed with 3.0% SE-30. Injector/column/detector temperatures were set at 120/60/120° C. and carrier $N_2$ gas flow rate at 30 ml/min. Peaks were intergrated by a Shimadzu CRIA microprocessor and enflurane concentrations calculated relative to the internal standard and standard calibration curves.

Statistical analyses were done by one-way analysis of variance for repeated measures and the differences between means were tested for significance using the Student-Newman-Keul's test at P value equal to or less than 0.05.

The delivery of the anesthetic in terms of inspired concentration was linear between minute volume of 15 and 25 liters/minute. Enflurane concentration increased with decreasing minute volume. As minute volume was reduced from 25 to 15 liters/minute, at an enflurane infusion rate of 3 ml/min., vaporized enflurane concentration increased from 3.67% to 5.36%. When minute volume was reduced from 25 to 15 l/min., at enflurane infusion rate of 1 ml/min. enflurane concentration increased from 1.20 to 1.90%.

Prior to administration of enflurane during HFJV, MAP was $123\pm3$ torr ($X\pm SEM$) with a cardiac index (CI) of $5.2\pm0.3$. Arterial blood gases indicated adequate ventilation with a $PaO_2$ of $493\pm19$ torr and a $PaCO_2$ of $32\pm1$ torr 5 min. after the administration of enflurane. MAP fell to $109\pm3$ torr and CI to $4.8\pm0.3$. After 15 min., MAP fell to $89\pm6$ torr and remained about the same level for up to 120 min. whereas CI remained at a level of 3.2 to 3.9. Arterial blood gases were relatively stable. Although there was a gradual rise in $PaCO_2$ in the first 15 min., it remained at about 36-38 torr thereafter. The time course of the changes in CI to parallel the increase in arterial blood enflurane which plateaued after 15 min. at about 20 to 30 mg%. At the end of anesthesia during HFJV, the animals could stand up within several minutes after enflurane was discontinued.

These test results clearly show that the anesthetic was delivered to the dogs effectively. A continuous amount of anesthetic was provided in relation to body weight. The presence of anesthetic in the blood was linear to the amount of anesthetic infused.

It will be appreciated that Applicant has provided a vaporizer that may be used with high-frequency jet ventilation for inhalation anesthesia.

The apparatus consists of a main tube or body which vaporizes inhalation anesthetic using the principle of airblast atomization. One side of the main body adapts to a connector of the endotracheal tube. A gas supply needle extends and is centered within the lumen of the main body and directed along the axis of the body. An inhalation anesthetic supply needle intersects the main body in general proximity to the gas supply needle. Preferably, the inhalation anesthetic supply needle intersects the main body in a generally perpendicular manner to the gas supply needle. Preferably, a scavenging tube intersects the main tube from below the main body and is generally preferably parallel to the inhalation anesthetic supply needle. The gas supply needle may be positioned horizontally and gas is jetted through it. At the point of intersection of the larger needle and the smaller needle airblast atomization occurs. Inhalation anesthetic is drawn up into the inhalation anesthetic supply needle by the negative pressure that is created by the high velocity flow of the gas at the tip of the smaller needle. A method of ventilating a patient is also disclosed which uses the vaporizer of the present invention.

Whereas particular embodiments of the invention have been described above for purposes of illustration, it will be evident to those skilled in the art that numerous variations of the details may be added without departing from the invention as defined in the appended claims.

I claim:

1. A vaporizer used for high-frequency jet ventilation comprising:
    a main body portion defining a passageway that extends therethrough and having an open end connectable to an endotracheal tube,
    a gas supply needle which extends into said passageway, and being operatively associated with a high-frequency jet ventilator for introducing said gas supply into said passageway of said main body portion at a desired frequency,
    an inhalation anesthetic supply needle operatively associated with infusion pump means for introducing liquid inhalation anesthetic fluid into said inhalation anesthetic supply needle at a controlled flow rate, and
    said inhalation anesthetic supply needle and said gas supply needle being disposed generally perpendicular relative to each other,
    said arrangement and the construction of said inhalation anesthetic needle and said gas supply needle being such that when a jet of gas is introduced into said passage-way the high velocity of said gas produces a negative pressure which draws said inhalation anesthetic fluid out of said inhalation anesthetic supply needle and airblast atomization occurs at the point of intersection of said gas from said gas supply needle and said fluid from said inhalation anesthetic supply needle whereby said fluid is reduced to small fluid droplets, said airblast atomization immediately followed by vaporization due to the increased surface area of said small droplets and further contact of said jet of gas with said droplets of said inhalation anesthetic such that a vaporized substance with only a gas phase containing molecules of said inhalation anesthetic exists in said passageway of said vaporizer with a controllable percentage of an inspired anesthetic concentration, and
    said construction of said passageway of said main body of said vaporizer being unobstructed along the path of travel of said vaporized gas such that said vaporized gas flows freely through said passageway out of said vaporizer into said endotracheal tube.

2. The vaporizer of claim 1, wherein said gas supply needle is generally larger in gauge than said inhalation anesthetic supply needle.

3. The vaporizer of claim 2, wherein said gas supply needle is about 8 to 14-gauge.

4. The vaporizer of claim 3, wherein said gas supply needle is about 14-gauge.

5. The vaporizer of claim 2, wherein said inhalation anesthetic supply needle is about 18 to 22-gauge.

6. The vaporizer of claim 5, wherein said inhalation anesthetic supply needle is about 20-gauge.

7. The vaporizer of claim 1, wherein the distance between said gas supply needle and said inhalation supply needle is about 0.3 to 1.0 millimeters.

8. The vaporizer of claim 7, wherein the distance between said gas supply needle and said inhalation anesthetic supply needle is 0.6 mm.

9. The vaporizer of claim 8, wherein said inhalation anesthetic is selected from the group consisting of enflurane, fluothane, and isoflurane.

10. The vaporizer of claim 9, wherein said inhalation anesthetic is enflurane.

11. The vaporizer of claim 1, including
a scavenging tube which is disposed generally perpendicular to the main body portion that contains a passageway that extends therethrough whereby a respirator may be attached to the end of said scavenging tube.

12. The vaporizer of claim 11, including a scavenging system for evacuation of exhaled gases.

13. The vaporizer of claim 12, including a respirometer means for measuring minute volume.

14. The vaporizer of claim 1, wherein the inside diameter of the passageway of said main body is about ⅜ inches.

15. The vaporizer of claim 1, including a window in the wall of said main body portion disposed near the tips of said gas supply needle and said inhalation anesthetic supply needle.

16. The vaporizer of claim 1, including pin means associated with said gas supply needle for stabilizing said gas supply needle.

17. The vaporizer of claim 1, including pin means associated with said inhalation anesthetic supply needle for stabilizing said inhalation anesthetic supply needle.

18. The vaporizer of claim 1, wherein the tip of said inhalation anesthetic supply needle is oriented generally aligned with the longitudinal axis of the center of the opening of said gas supply needle.

19. The vaporizer of claim 18, wherein the center of the opening of said inhalation anesthetic supply needle is positioned within half of the radius of said gas supply needle.

20. The vaporizer of claim 1, wherein the distance between said needles may be adjusted by adjustment means.

21. The vaporizer of claim 1, including a reinspired gas tube for providing access for reinspired gases into said main body passageway.

22. A method of ventilating the lungs of a patient comprising:
providing a vaporizer having a main body portion defining a passageway, and a gas supply needle and an inhalation anesthetic supply needle, the tips of each said needle being disposed generally perpendicular relative to each other in said passageway,
jetting gas through said gas supply needle by means of a high frequency jet ventilator and introducing said gas into said main body portion of said vaporizer at a desired frequency,
infusing an inhalation anesthetic fluid through said inhalation anesthetic supply needle at a controlled flow rate,
causing airblast atomization to occur at the point of intersection of said gas from said gas supply needle and said fluid from said inhalation anesthetic supply needle, whereby said fluid is reduced to small fluid droplets, said airblast atomization being a result of the high velocity of said jetting of said gas producing a negative pressure which draws said inhalation anesthetic fluid out of said tip of said inhalation anesthetic supply needle, thereby entraining said fluid into the stream of gas in said passageway of said body portion of said vaporizer,
after said airblast atomization, immediately causing vaporization of said entrained anesthetic fluid in said passageway prior to the introduction of the resultant vaporized gas into the lungs of a patient, and
for said vaporization step, causing further contact of said jet of gas with said small droplets of said inhalation anesthetic such that a vaporized substance with only a gas phase containing molecules of said inhalation anesthetic exists in said passageway of said vaporizer with a controllable percentage of inspired anesthetic concentration, and causing said vaporized gas to flow freely along its path of travel through said passageway in said vaporizer without any obstructions and into the lungs of said patient.

23. The method of claim 22, including infusing said inhalation anesthetic through said inhalation anesthetic supply needle by means of an infusion pump means.

24. The method of claim 23, including employing enflurance as said inhalation anesthetic.

25. The method of claim 22, including measuring minute volume by means of respirometer means.

26. The method of claim 25, including evacuating expired gases by means of scavenging means.

27. The method of claim 22, including providing a reinspired gas tube for accessing expired gases into said passageway.

28. The method of claim 22, including providing 8 to 14-gauge needles as said gas supply needles and 18 to 22-gauge needles as said inhalation anesthetic supply needles.

29. The method of claim 28, including providing a 14-gauge needle as said gas supply needle and a 20-gauge needle as said inhalation anesthetic supply needle.

30. The method of claim 29, including employing a distance of about 0.3 to 1.0 mm between said needles.

31. The method of claim 30, including employing a distance of 0.6 mm between said needles.

32. The method of claim 31, including stabilizing said first and said second needles by means of stabilizing means.

33. The method of claim 22, including measuring the concentration of expired gases by means of mass spectrometer means.

* * * * *

UNITED STATES PATENT AND TRADEMARK OFFICE
CERTIFICATE OF CORRECTION

PATENT NO. : 5,072,726
DATED : December 17, 1991
INVENTOR(S) : MANOOCHEHR MAZLOOMDOOST, and WILFRED L. FOON It is certified that error appears in the above-identified patent and that said Letters Patent is hereby corrected as shown below:

Column 1, line 36, --for-- should be inserted after --tent--.

Column 6, line 62-63, --prostigmine and 0.4 mg atropine at the end of the studies.-- should be inserted after "1mg".

Column 7, line 35, --appear-- should be inserted after "CI".

Claim 24, column 10, line 34, "enflurance" should be --enflurane--.

Signed and Sealed this

Second Day of August, 1994

Attest:

BRUCE LEHMAN

Attesting Officer

Commissioner of Patents and Trademarks